United States Patent [19]

Brady et al.

[11] 4,396,555
[45] Aug. 2, 1983

[54] PARTIAL ESTERS OF POLYPHOSPHORIC ACID

[75] Inventors: Thomas P. Brady, Holliston; Horst G. Langer, Wayland, both of Mass.

[73] Assignee: The Dow Chemical Company, Midland, Mich.

[21] Appl. No.: 299,276

[22] Filed: Sep. 4, 1981

Related U.S. Application Data

[63] Continuation of Ser. No. 119,057, Feb. 6, 1980, abandoned.

[51] Int. Cl.$^3$ .............................................. C07F 9/08
[52] U.S. Cl. .................................. 260/933; 260/980; 427/440
[58] Field of Search .......................................... 260/933

[56] References Cited

U.S. PATENT DOCUMENTS

| | | | |
|---|---|---|---|
| 2,503,204 | 4/1950 | Kosolapoff | 260/933 |
| 2,947,774 | 8/1960 | Levine et al. | 260/933 |
| 3,062,858 | 11/1962 | Cramer et al. | 260/933 |
| 3,150,039 | 9/1964 | Lanham et al. | 260/933 |
| 4,301,025 | 11/1981 | Brady et al. | 260/933 X |

FOREIGN PATENT DOCUMENTS 869765 2/1979 Belgium.
2013643 8/1979 United Kingdom ................ 260/933

OTHER PUBLICATIONS

Van Waser, "Phosphorus and its Compounds," vol. 1, (1958), pp. 632–633 & 659–660.
Roseman et al., "J. A.C.S.," vol. 83, (1961), pp. 659–663.
Nassbaum et al., "Tetrahedron Letters," vol. 20, (1964), pp. 2467–2472.
Furukawa et al., "Chem. Pham. Bull. Japan," vol. 13, (1965), pp. 16–21.
Kochetov et al., "Tetrahedron Letters," vol. 16, (1963), pp. 1207–1218.

*Primary Examiner*—Anton H. Sutto
*Attorney, Agent, or Firm*—Douglas N. Deline

[57] ABSTRACT

Glycol ether partial esters of the formula

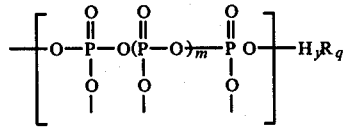

where R is a specified substituent formed by reaction of monohydroxyl reactants of (poly)glycols with phosphorus pentoxide.

6 Claims, No Drawings

PARTIAL ESTERS OF POLYPHOSPHORIC ACID

CROSS-REFERENCE TO RELATED APPLICATION

This is a continuation of application Ser. No. 119,057, filed Feb. 6, 1980, now abandoned.

BACKGROUND OF THE INVENTION

The invention relates to novel partial esters of polyphosphoric acids such as diphosphoric acid. Previously known partial esters have not been stable due to hydrolytic decomposition resulting in formation of monophosphoric acid esters.

In U.S. Pat. Nos. 2,866,680 and 2,947,774 the formation of certain alkyl esters of di- and polyphosphates are described. The compounds were unstable and decomposed within hours or at best after a few days if refrigerated.

In U.S. Pat. No. 3,004,056, surface-active monophosphates are formed by gradual addition of solid $P_2O_5$ to an excess of polyoxyalkylene ether with vigorous agitation. The specification teaches that addition of the hydroxyl compound to the $P_2O_5$ is inadvisable since a tar is formed thereby and the reaction will not proceed to completion.

SUMMARY OF THE INVENTION

According to the instant invention are provided polyphosphoric acid partial esters of the formula $$\left[ \begin{array}{c} O \\ \parallel \\ -O-P-O(P-O)_m-P-O \\ | \quad | \quad | \\ O \quad O \quad O \\ | \quad | \quad | \end{array} \right] H_y R_q \quad I$$

wherein R is each occurrence a remnant formed by removal of a hydroxyl from a monohydroxyl compound selected from (a) a (poly)alkylene glycol monoether of the formula $$HO \!-\!\! (CH_2CHO)_n R_2$$
$$\quad\quad\quad\quad | \\ \quad\quad\quad\quad R_1$$

where $R_1$ is hydrogen, methyl, or halomethyl; $R_2$ is $C_{1-6}$ alkyl or haloalkyl, phenyl, halophenyl or methylphenyl; n is an integer from 1 to 4;

(b) a phenol or halophenol; and (c) a $C_{1-20}$ aliphatic or halogenated aliphatic monohydroxyl compound;

provided that in at least one occurrence R is selected from (a); m is an integer from zero to three, y is an integer from one to three, and q is equal to $m+4-y$.

The monoethers of alkylene and (poly)alkylene glycols of the previously described formula suitably include for example methyl, ethyl, propyl, n-butyl or tertiary-butyl ethers of ethylene glycol, propylene glycol, (poly)ethylene or (poly)propylene glycols.

The phenol or halophenols include for example mono- and polyhalogenated phenols such as chloro- and bromophenols.

The $C_{1-20}$ aliphatic monohydroxyl compounds include common alkanols and halogenated derivatives thereof and unsaturated monohydroxyl compounds such as hydroxy-substituted alkenes, alkynes and halogenated derivatives thereof.

Preferred are diesters of diphosphoric acid, compounds of formula I wherein m is zero, R is selected from (a), and q and y are both two.

The compounds or neutral ammonium or alkali metal derivatives thereof are useful as corrosion inhibitors for functional fluids such as heat and pressure transmission fluids, and as fire-retarding agents for cellulosic materials.

DETAILED DESCRIPTION OF THE INVENTION

The invented compounds may be formed by the reaction of a monoether of a (poly)alkylene glycol optionally in combination with the phenol, halophenol or $C_{1-20}$ aliphatic or halogenated aliphatic monohydroxyl compounds with phosphorus pentoxide. Alternatively the monohydroxyl compounds may be reacted in sequence. Remnant acid functionality is assured by reacting a stoichiometrically limited amount of the monohydroxyl compound. Preferably in order to assure the presence of at least some (poly)alkylene glycol monoether remnant in each molecule of the reaction product, at least one quarter mole of (poly)alkylene glycol monoether is reacted with each mole of $P_2O_5$. The reaction technique is well-known being similar to that disclosed in U.S. Pat. No. 2,866,680. Accordingly, the monohydroxyl reactant is controllably added to a slurry comprising phosphorus pentoxide and an organic solvent such as the lower alkanes, aromatics, or halogenated hydrocarbons. A preferred solvent is dichloromethane.

To compensate for possible water contamination of the monohydroxyl reactant, excess $P_2O_5$ is preferably utilized. The ratio of monohydroxyl compound remnant to phosphorus in the reaction product is desirably about 1:1.

The exothermic reaction causes heating of the reaction mass. Proper choice of a solvent allows the reaction to be maintained at a gentle reflux at moderately elevated temperatures less than about 150° C. The reaction may be continued for several hours or longer until the $P_2O_5$ is substantially completely reacted. Additional heating during the course of the reaction may be accomplished by conventional means.

The product, generally a light colored liquid, may be separated from any excess unreacted $P_2O_5$ by decanting or filtration, and the solvent removed if desired by evaporation or other technique.

When prepared according to the foregoing process, the resulting reaction product is obtained in high yield. Contaminants consist primarily of monophosphate reaction products, present preferably in an amount less than 10 percent by weight. Purification of the desired reaction product may be easily accomplished by chromatographic separation techniques well-known in the art. For most applications however, such purification techniques are not desired and minor contamination with reactants and monophosphate esters is acceptable. Preferably the product comprises at least 75 percent, most preferably at least 90 percent of the polyphosphoric acid partial esters of formula I.

Because the hydroxyl and alkoxy moieties of the invented compounds are known to be labile, the reaction product is more correctly described as an equilibrium mixture of compounds of generic formula I. Individual components of such mixture may have more or less than two hydroxyl moieties but on average the product mixture maintains an R:P ratio of about 1:1. When added to hydroxyl- or monoether-containing solvents, such as may commonly be found in functional fluids, the product may for this same reason exist in an equilibrium mixture. For example, interchange of alkyl monoether moieties is observed when the monoether-containing solvent is different from that employed in the initial formation of the compounds.

SPECIFIC EMBODIMENTS

The following examples are provided as further illustrative of the present invention and are not be be construed as limiting.

EXAMPLE 1

To a reaction flask containing 500 ml $CH_2Cl_2$ under nitrogen atmosphere, phosphorus pentoxide (270 g, 1.9 moles reagent grade) was added with stirring. Over approximately 2 hours ethylene glycol n-butyl ether (425 g, 3.6 moles reagent grade) was added from a dropping funnel. The reaction caused gentle reflux. After complete addition only a small amount of unreacted $P_2O_5$ remained and the flask contained a clear yellow colored solution. Analysis by $^{31}P$ nuclear magnetic resonance spectroscopy indicated the product comprised greater than 90 percent of the diphosphoric acid half ester with minor amounts of other partial esters of polyphosphoric acids, plus monophosphates and full ester contaminants.

EXAMPLE 2

The reaction conditions of Example 1 were repeated except that the glycol ether utilized was 1-methoxy-2-propanol added to $P_2O_5$ in a molar ratio of about 1.9:1. The product recovered was primarily the diester of diphosphoric acid having the empirical formula $H_2P_2O_5(OCH(CH_3)CH_2OCH_3)_2$.

EXAMPLE 3

A portion of the product produced in Example 1 was neutralized by bubbling dry $NH_3$ into the solution at a rate sufficient to cause a gentle reflux. After about 90 minutes no further exotherm occurred indicating the reaction was complete. The solution was further diluted with $CH_2Cl_2$ to a concentration of 15 percent by weight and used to treat several small strips of $\frac{1}{4}''$ fir plywood, $\frac{1}{2}''$ wide and 3" long. After immersion in the solution for between 2 and 8 hours, the strips were dried at 100° C. for about 4 hours and humidified at normal room conditions for two days. When clamped at a 45° angle and ignited for 15 seconds with a bunsen flame, all the treated strips self-extinguished in an average of less than 20 seconds. By comparison, untreated strips subjected to the same procedure are entirely consumed.

What is claimed is:

1. Polyphosphoric acid partial esters of the formula

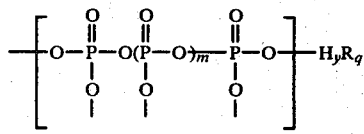

wherein
R is each occurrence a remnant formed by removal of a hydroxyl from a monohydroxyl compound selected from the group consisting of
(a) a (poly)glycol monoether of the formula

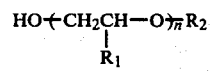

wherein $R_1$ is hydrogen, methyl, or halomethyl; $R_2$ is $C_{1-6}$ alkyl or haloalkyl, phenyl, halophenyl or methylphenyl; and n is a number from 1 to 4;
(b) a phenol or halophenol; and
(c) a $C_{1-20}$ alkanol or hydrogenated alkanol;
provided that in at least one occurrence R is selected from (a); m is an integer from zero to three, y is an integer from one to three and q is equal to $m+4-y$.

2. Polyphosphoric acid partial esters of claim 1 wherein R is each occurrence selected from (a).

3. The polyphosphoric acid partial esters of claim 2 wherein m is zero and both y and q equal 2.

4. The polyphosphoric acid partial esters of claim 3 wherein $R_1$ is hydrogen.

5. The polyphosphoric acid partial esters of claim 4 wherein R is butoxyethyl.

6. A composition of matter containing polyphosphoric acid partial esters of claim 2 or 3 in an amount of at least 90 percent by weight which is formed by contacting a (poly)glycol monoether of the formula

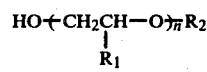

wherein $R_1$ is hydrogen, methyl, or halomethyl; $R_2$ is $C_{1-6}$ alkyl or haloalkyl, phenyl, halophenyl or methylphenyl; and n is a number from 1 to 4; with a slurry comprising phosphorus pentoxide and an organic solvent at a temperature less than 150° C. and thereafter removing the organic solvent to recover the composition.

* * * * *